(12) United States Patent
Ostgard et al.

(10) Patent No.: US 6,649,799 B2
(45) Date of Patent: Nov. 18, 2003

(54) METHOD FOR PRODUCING PRIMARY AND SECONDARY AMINES BY HYDROGENATION OF NITRILES AND IMINES

(75) Inventors: Daniel Ostgard, Kleinostheim (DE); Monika Berweiler, Maintal (DE); Stefan Röder, Sinntal (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 10/024,488

(22) Filed: Dec. 21, 2001

(65) Prior Publication Data

US 2002/0173676 A1 Nov. 21, 2002

(30) Foreign Application Priority Data

Dec. 23, 2000 (DE) .......................................... 100 65 031

(51) Int. Cl.⁷ ..................... C07C 209/34; C07C 209/36
(52) U.S. Cl. ..................... 564/385; 564/492; 564/493
(58) Field of Search ................................ 564/385, 492, 564/493

(56) References Cited

U.S. PATENT DOCUMENTS 5,840,989 A   11/1998   Cordier et al.
6,337,300 B1   1/2002   Sauer et al.

FOREIGN PATENT DOCUMENTS

EP   1 068 900 A1   1/2001

OTHER PUBLICATIONS

Database CAPLUS on STN, Acc. No. 1976:425897, Haase et al., DD 117617, abstract.*
Database CAPLUS on STN, Acc. No. 1981:128179, Yamada et al., EP 19674, abstract.*
International Search Report, dated Jun. 24, 2002, for PCT Application No. PCT/EP01/15268, 6 pps.

* cited by examiner

Primary Examiner—Brian Davis
(74) Attorney, Agent, or Firm—Smith, Gambrell & Russell, LLP

(57) ABSTRACT

A method for producing amines by catalytic hydrogenation of nitrites or imines with hydrogen-containing gases in the presence of a molded hydrogenation catalyst of Raney type, where the Raney catalyst is in the form of hollow bodies.

43 Claims, No Drawings

METHOD FOR PRODUCING PRIMARY AND SECONDARY AMINES BY HYDROGENATION OF NITRILES AND IMINES

INTRODUCTION AND BACKGROUND

The invention is directed toward an improved method for producing primary and/or secondary amines from imines and nitrites, which includes the catalytic hydrogenation of nitriles or imines with hydrogen or hydrogen-containing gases in the presence of a molded hydrogenation catalyst of Raney type. The invention includes in particular the production of monoamines and diamines and the production of aminonitriles. The method allows the use of distinctly lower amounts of catalyst in the production of the amines while having the same or higher yields than with the previously known methods.

Nitriles can be catalytically reduced to amines with hydrogen. As is known, in this hydrogenation the intermediate step usually goes through an imine. For this reason one can assume that the hydrogenation of nitrites always also includes the hydrogenation of imines.

Amines are a decidedly important class of substances in organic chemistry. For example, they serve as starting materials for the production of solvents, surfactants, bactericides, anticorrosion agents, foam suppression agents, additives, pharmaceuticals or dyes. Moreover, they are very important in the production of polyamide and polyurethane plastics.

In the production of amines by hydrogenation of nitrites and imines Raney catalysts are frequently preferred because of their good catalytic properties and the fact that they are considerably easier to make than supported catalysts. Raney catalysts, which are also called activated metal catalysts, consist of an alloy of at least one catalytically active metal and at least one metal that can be leached with alkalis. Chiefly aluminum is used for the alkali-soluble alloy component, but other metals such as zinc and silicon can also be used. By adding alkalis to the alloy the leachable component is dissolved out, due to which the catalyst becomes activated.

Many inventions for production of amines from nitriles or imines by catalytic hydrogenation with Raney catalysts are known. Here different Raney catalysts, more precisely catalysts with different active metals or metal combinations, are used, in each case according to the process.

For example, U.S. Pat. No. 5,777,166 describes a method for hydrogenation of nitrites to amines using doped and alcoholate-treated Raney nickel catalysts. It is clear from the examples that the described method is preferably carried out in a batch process using catalysts in powder form. In contrast, DE 223 81 53 describes the hydrogenation of fatty acid nitriles to fatty acid amines by means of cobalt catalysts. In this process, too, the hydrogenation is carried out with the aid of powdered Raney catalysts.

Catalysts of Raney type in powder form have the disadvantage that they can only be used in a batch process and after the catalytic conversion have to be separated from the reaction medium, at high cost. For this reason among others, it is preferred to produce amines by hydrogenation of nitrites and imines using molded Raney catalysts and as far as possible to carry out this production in a continuous process. Fixed bed catalysts that, besides having good catalytic activity, also have to have sufficient strength for continuous operation, are needed for this purpose.

Combinations of metals are also known in Raney catalysts. U.S. Pat. No. 6,087,296 describes a method for hydrogenation of unsaturated organic compounds using a Raney catalyst that can contain iron, cobalt and other metals and promoters.

DE Patent 195 40 191 describes a two-step method for producing isophoronediamine. In this process isophorone is first converted with ammonia to isophoronenitrileimine in the presence or absence of an imination catalyst and the resulting product mixture is hydrogenated to isophorphonediamine while adding hydrogen. Isophoronenitrileimine contains both a hydrogenatable cyano group and a hydrogenatable imino group. A molded Raney catalyst based on cobalt serves as hydrogenation catalyst. The catalyst contains, besides the catalyst alloy of cobalt and aluminum, additional metallic cobalt, which serves as a binder to produce the necessary stability of the molded article. The disadvantage of this method lies in that the cobalt added as binder has only slight catalytic activity, so that the activity of the catalyst is reduced in comparison with binder-free catalysts. In this way it is necessary to use relatively high amounts of catalysts in order to achieve good product yields.

This disadvantage is avoided in the production of isophoronediamine as described in EP 0 880 996. A molded cobalt catalyst of Raney type, which before activation by leaching out the aluminum consists exclusively of a cobalt-aluminum alloy, is used for hydrogenation. This catalyst has the advantage over the catalyst used in DE 19540191 that it has a distinctly lower bulk density of only 1.2 kg/L. In spite of the lower bulk density hydrogenation with the catalyst consisting only of the catalyst alloy leads to slightly higher yields for the same catalyst weight. The disadvantage of the method described in EP 0 880 996 lies in the fact that the catalyst that is used still has quite high bulk densities relative to fixed bed catalysts that are not of Raney type.

DE 199 33 450.1 describes metal catalysts that are in the form of hollow bodies, preferably in the form of hollow spheres. These catalysts have a low bulk density, from 0.3 to 1.3 g/mL. Besides the catalysts, their use in hydrogenation reactions is also claimed. The examples give activity tests for the hydrogenation of nitrobenzene to aniline, in which the hydrogen uptake and thus the activity of the catalyst per gram of catalyst is clearly higher when the hollow spherical catalysts are used than with comparison catalyst. The use of the described catalysts for the production of amines by hydrogenation of nitrites and imines, however, is not mentioned.

For this reason the task of this invention was to develop a method for producing amines from nitrites and imines by catalytic hydrogenation, in which the hydrogenation is carried out with a molded hydrogenation catalyst of Raney type that, while having a catalytically active layer of sufficient strength and considerably lower bulk density than comparable catalysts, has the same or better hydrogenation activity than the previously used catalysts. Another goal of the invention is to achieve the same or better starting material conversion rates than with the known methods while using less catalyst material.

SUMMARY OF THE INVENTION

The underlying invention showed that the production of amines by hydrogenation of imines or nitrites by means of the hollow Raney catalysts described in DE 199 33 450.1 is possible with clearly higher conversion rates per unit of weight of catalyst than with comparable catalysts. This observation is surprising in that one cannot necessarily assume that the hollow Raney catalysts will achieve the necessary activities in the particular case of the hydrogenation of imines and nitrites.

The invention thus consists of a method for producing amines by catalytic hydrogenation of imines and/or nitrites, in which a molded Raney catalyst is used as hydrogenation catalyst, which is characterized by the fact that the Raney catalyst is in the form of hollow bodies. This method has the advantage that imines can be produced with the same or higher yields while using clearly smaller amounts of catalyst than is possible up to now according to the prior art.

The advantage underlying this invention is achieved through the use of Raney catalysts in the form of hollow bodies. The production of the catalysts used in the method in accordance with the invention can be carried out in correspondence with the method described in DE 199 33 450.1. According to this method a mixture of an alloy powder of a catalytically active metal with a leachable metal, preferably aluminum, an organic binder and optionally an inorganic binder, water and promoters is applied to spheres that consist of a thermally removable material. Preferably, polystyrene foam spheres can be used. The application of the mixture containing the metal alloy to the polymer spheres can preferably be carried out in a fluidized bed. Preferably 0–10 wt % polyvinyl alcohol and/or 0–3 wt % glycerol can be used as organic binders. The coated polymer foam spheres are then calcined above 300° C., preferably in a range between 450 and 1300° C., in order to remove the polymer foam thermally and to sinter the metal. In this way the hollow spheres obtain a stable shape. After calcination the hollow catalysts are activated by treatment with basic solutions, preferably alkali or alkaline earth hydroxides in water, more preferably aqueous sodium hydroxide. The resulting catalysts have bulk densities between 0.3 and 1.3 kg/L.

The Raney catalysts used in the method in accordance with the invention preferably contain nickel, cobalt, copper, iron, palladium, platinum, ruthenium or mixtures of these metals as catalytically active components. Preferably, Raney catalysts that have been activated by leaching out of aluminum, silicon and/or zinc, especially aluminum, by means of alkalis are used in the production of amines in accordance with the invention.

DETAILED DESCRIPTION OF THE INVENTION

In accordance with the invention, the catalysts used in the method have the shape of hollow bodies. In a preferred embodiment the Raney catalyst are in the form of hollow spheres. Hollow spheres are usually easy to make and have high resistance to breakage.

The hollow catalysts used in accordance with the invention can contain a binder. The binder enables the catalyst hollow bodies to have greater strength, which is necessary because of their hollow form. Preferably, powders of the metals that are also contained in the catalyst alloy as catalytically active components are used as binders in the production of the catalyst hollow bodies. However, it is also possible to add other binders, especially other metals, as binders. If cobalt catalysts are used in accordance with the invention for production of amines, these catalysts are preferably used without binders. Hollow cobalt catalysts have sufficient strength even without added binders.

The catalyst alloy of the catalysts used in accordance with the invention is preferably composed of up to 20–80 wt % of one or more catalytically active metals and up to 20–80 wt % of one or more alkali-leachable metals, preferably aluminum. A fast or slow cooled alloy can be used as catalyst alloy. Fast cooling is understood to mean, for example, cooling at a rate from 10 to $10^5$ K/sec. The cooling media can be various gases or liquids such as water. Slow cooling is understood to mean methods with lower cooling rates.

Hollow Raney catalysts doped with other metals can be used in the method in accordance with the invention. The doping metals are frequently also called promoters. The doping of Raney catalysts is described, for example, in the documents U.S. Pat. No. 4,153,578, DE 21 01 856, DE 21 00 373 or DE 20 53 799. Preferred elements for doping are elements of groups 1A, 2A, 3B through 7B, 8, 1B, 2B and 3A of the periodic system and germanium, tin, lead, antimony and bismuth. Particularly preferred are chromium, manganese, iron, vanadium, tantalum, titanium, tungsten, molybdenum, rhenium and/or metals of the platinum group. The amount of promoters in the catalyst can preferably be 0–20 wt %. The promoters can already be contained as an alloy component, or can be added only later, especially after activation.

In the method in accordance with the invention preferably hollow catalysts with a diameter from 0.05 to 20 mm and a shell thickness from 0.05 to 7 mm are used. The catalyst shells can be impermeable, or they can have a porosity of 80% and higher.

In the method in accordance with the invention hollow catalysts that consist of one or more layers can be used. If the catalysts have more than one layer, the catalyst bodies are dried between the individual coating steps in producing them. This is preferably carried out in a fluidized bed at temperatures from 60 to 150° C. It is also possible to make a hollow catalyst with several layers where it is not dried between the individual coating steps.

The hollow Raney catalysts are used in activated state in the method in accordance with the invention. The leachable metal present in the unactivated catalyst particles can, in the activated state, have been leached out with alkalis entirely or only partly in the activated state.

Extrudates, granulates, fiber tablets or shell-activated tablets can also be preferred for exothermic reactions, because of their good heat exchange properties, in the method in accordance with the invention.

According to the method in accordance with the invention aliphatic and aromatic amines can be produced from the underlying nitrites or imines. The amines can be primary or secondary amines. The amines can be compounds of the general formula $$R^1R^2CH\text{---}NHR^3$$

where $R^1$, $R^2$ and $R^3$, independent of one another, are aliphatic and/or aromatic, unbranched and/or branched, substituted and/or unsubstituted, saturated and/or unsaturated residues or hydrogen. If $R^3$ is not hydrogen, a ketimine or aldimine is the starting material for the method in accordance with the invention. If $R^3$=H, the starting material can be a nitrile, a ketimine or aldimine. The amines produced in accordance with the invention can be open-chain, alicyclic or aromatic.

Preferred amines are compounds in which $R^1$=$H_3C$ 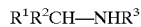$(CH_2)_n$, with n=1 to 30, and $R^2$ and $R^3$ meaning hydrogen. Examples are ethylamine, n-propylamine, n-butylamine, n-pentylamine, n-hexylamine, n-heptylamine, n-octylamine, n-nonylamine or n-decylamine. These amines can be produced both from the underlying nitriles $R^1$—CN and from the underlying imines $R^1HC=NH$, with $R^1=H_3C$—$(CH_2)_n$ (n=1).

The residues $R^1$, $R^2$ or $R^3$ can be substituted residues. They can be substituted with residues that themselves can also be hydrogenated in the hydrogenation underlying the method in accordance with the invention or that are not subject to hydrogenation. In the case that the amines are supposed to be substituted with hydrogenatable groups at the residues $R^1$, $R^2$ or $R^3$, the reaction conditions should be chosen so that chiefly the cyano group, or the imino group, is hydrogenated. Examples of possible substituents are R=F, Cl, Br, I, $NO_2$, $NH_2$, HO, CN, alkyl, aryl, alkenyl, alkynyl, O=C, HOOC, $H_2NOC$, ROOC, RO with R=alkyl, aryl, alkenyl or alkynyl. The amines produced in accordance with the invention can contain one or more of these substituents. It is also possible that the substituents themselves are again substituted with one of the listed substituents. It is thus possible, for example, to produce diamines, polyamines and/or aminonitriles by the method in accordance with the invention. A particularly preferred embodiment of the invention is a method for producing aliphatic α, ω-diamines of the general formula $H_2N$—$CH_2$—$(CH_2)m$—$CH_2$—$NH_2$, in which m is a whole number between 1 and 12, especially 2, 3, 4, 5 or 6, such as, for example, tetramethylenediamine, pentamethylenediamine, hexamethylenediamine, heptamethylenediamine, octamethylenediamine or decamethylenediamine.

A likewise preferred embodiment of the invention is a method for producing aliphatic ω-amino-α-nitriles of the general formula NC—$(CH_2)_m$—$CH_2$—$NH_2$, in which m is a whole number between 1 and 12, especially 2, 3, 4, 5 or 6, such as, for example, ω-aminobutyronitrile, ω-aminovalerionitrile, ω-aminocapronitrile, ω-aminoheptanoic acid nitrile or co-aminooctanoic acid nitrile.

It is also possible, for example, in the production of isophoronediamine, to start from a compound that contains one or more nitrilo groups and at the same time one or more imino groups. These compounds can be converted to the corresponding diamines or polyamines by the method in accordance with the invention.

A likewise preferred embodiment of the invention is a method for producing methylamines substituted with aromatic residues. The aromatic residues themselves can likewise be substituted with one or more residues R, where R=F, Cl, Br, I, $NO_2$, $NH_2$, HO, CN, alkyl, aryl, alkenyl, alkynyl, O=C, HOOC, $H_2NOC$, ROOC, RO with R=alkyl, aryl, alkenyl or alkynyl. For example, benzylamine, methylbenzylamine or (3-chlorophenyl)methylamine can be produced with the method in accordance with the invention.

A likewise preferred embodiment of the invention is a method for producing fluorinated, chlorinated, brominated or iodinated mono- or polyamines.

Ethylamine, n-propylamine, n-butylamine, n-pentylamine, n-hexylamine, n-heptylamine, n-octylamine, n-nonylamine, n-decylamine, stearylamine, pentenylamine, butynylamine, chloroethylamine, trichloroethylamine, hydroxyethylamine, 3-methoxypropylamine, 1,3-bis(3-aminopropyloxy)-2-propanol, tris(3-aminopropyl) nitromethane, 4-(N,N-dimethylamino)butylamine, 4-(N,N-diethylamino)butylamine, di(3-aminopropyl)ether phenylethylamine, (2-chlorophenyl)methylamine, (2,6-dichlorophenyl)methylamine, 1,3-bis(aminomethyl) benzene, 3-(aminomethyl)benzonitrile, 4-bis(aminomethyl) benzene, 4-(aminomethyl)benzonitrile or isophoronediamine can especially preferably be produced by the method in accordance with the invention.

In accordance with the invention it is possible to produce only one amine in a reaction. However, it is also possible to produce mixtures of different amines by the method in accordance with the invention. These amines can, for example, be obtained by nonselective hydrogenation of starting substances that contain several hydrogenatable cyano or imino groups or by hydrogenation of mixtures that contain two or more nitrites and/or imines.

The method in accordance with the invention can be carried out with hydrogen as hydrogenation gas or with gas mixtures that contain hydrogenation, for example, a mixture of hydrogen and carbon monoxide and/or carbon dioxide. In order to avoid possible poisoning of the catalyst, it is preferable to conduct the method in accordance with the invention with gases or gas mixtures that contains at least 95%, preferably at least 99% hydrogen.

It is possible to carry out the method in accordance with the invention in the liquid phase or in the gas phase.

The method in accordance with the invention can be carried out batchwise or continuously. In a continuous process the reactor can be operated in a soaking bed or trickle bed process, with the trickle bed process being preferred. In the preferred case of a continuous process a mixture of at least the nitrile and/or imine and hydrogen is sent to the top of the reactor. If the method is carried out batchwise, it proved to be advantageous to position the catalyst in a catalyst basket in the reactor, so that the substances to be hydrogenated or the mixture containing the substances to be hydrogenated can flow intimately through the catalyst.

However, independent of the process mode, it proved to be advantageous to add one or more solvents to the reaction mixture. The usual solvents can be, for example liquid ammonia, aqueous ammonia, amines, diamines or triamines with 1–6 carbon atoms, aliphatic alcohols with 1–4 carbon atoms, ethers or hydrocarbons with 4–10 carbon atoms. Examples of suitable solvents are methanol, ethanol, triethylamine, trimethylamine, tripropylamine, tributylamine, ammonia or hexane. The presence of one or more solvents can on the one hand result in the operating parameters like pressure and temperature lying in more moderate ranges than when the process is carried out without solvents. On the other hand, the selectivity of the hydrogenation reaction can be controlled by the proper choice of solvents. This is important especially when, besides the nitrilo groups or imino groups there are other groups in the starting molecule that are subjected to hydrogenation or in the production of cyano amines from dinitriles, in which only one nitrilo group of the starting compound is supposed to be hydrogenated. The solvent(s) is/are usually added in a weight ratio from 1:1 to 10:1 with respect to the weight of the nitrile or imine that is used. However, it is also possible to conduct the reaction in the absence of a solvent or with amounts of solvents greater than indicated above.

Usually the hydrogenation carried out in accordance with the invention can be operated in the presence of a solvent at a pressure in the range from 0.3 to 15 MPa. The usual temperatures at which the reaction is carried out in the liquid phase lie in the range from 20 to 150° C., preferably in the range from 30 to 100° C. As a rule this is dependent on the nitrites or imines from which the desired amine is to be produced and whether a complete or only partial hydrogenation, as, for example, in the production of ω-aminocapronitrile, is supposed to be achieved. Higher temperatures can be used when the reaction is carried out in the gas phase.

The residence times of the compound to be hydrogenated at the catalyst is highly dependent on which catalyst is to be used for which particular reaction and on whether a complete or only partial hydrogenation of the starting compound is to be achieved. Usually, the catalyst loads lie in a range between 0.01 and 15 kg, preferably between 1 and 5 kg of nitrile, or imine, per kg of catalyst per hour. Especially when only a partial hydrogenation is desired, the selectivity of the reaction can be controlled by adjusting the catalyst load [LHSV, WASV].

The hydrogen content in the reaction mixture is likewise highly dependent on the relevant compound to be hydrogenated and the desired degree of hydrogenation of the product compound. Usually hydrogen is used in a mol ratio from 1:1 to 300:1 with respect to the amount of nitrile or imine that is used. For example, in the production of isophoronediamine it can be preferable to use hydrogen in a 1:1 mol ratio with respect to the amount of isophoronenitrilimide that is used, in the presence of ammonia and methanol as solvents. In contrast, with other compounds it can be advantageous to use an excess amount of hydrogen.

Independent of whether the method in accordance with the invention for producing amines is carried out in a preferred embodiment or not, basic compounds, preferably one or more hydroxide bases, can be added to the reaction mixture in the hydrogenation of the imines or nitrites. The addition of hydroxide bases can increase the yield of amines and/or increase the purity of the product amines. A frequent side reaction in the hydrogenation of nitriles and imines is the formation of secondary amines. This is caused by an exchange of the imino function, in which the already formed primary amine forms a new n-alkylated imine in the ongoing intermediate imine or from the starting imine through displacement of ammonia or an amine and this n-alkylated imine then becomes hydrogenated further to a secondary amine. It is this side reaction in particular that is reduced or nearly completely suppressed through the addition of bases.

Suitable hydroxide bases are, for example, alkali hydroxides, alkaline earth hydroxides or ammonium hydroxides. Particularly preferred hydroxide bases are quaternary ammonium hydroxides. Suitable ammonium hydroxides are ones of the general formula $(R^4R^5R^6R^7N)^+ OH^-$, where $R^4$ to $R^7$ can be the same or different and stand for aliphatic, cycloaliphatic or aromatic residues. Preferred examples are tetramethylammonium hydroxide, tetraethylammonium hydroxide, tetra-n-propylammonium hydroxide and tetra-n-butylammonium hydroxide. Suitable concentrations are 0.01–100 mmol, preferably 0.2–20 mmol of a tetraalkylammonium hydroxide per mol of the isophoronenitrile.

Depending on the catalyst that is used, the compound to be hydrogenated and the reaction parameters it may be preferable for the ammonia to be present during the hydrogenation. The ammonia that is present can contribute to making the reaction more selective or to reducing the formation of byproducts or suppressing them nearly completely. The usual amounts of ammonia are 0–80 wt % with respect to the entire mixture that is subjected to hydrogenation. If a positive effect is not achieved by the addition of ammonia or if there is only a little byproduct formation, preferably the addition of ammonia can be omitted. For example, in many cases the addition of ammonia is not necessary when using cobalt catalysts.

It is also possible to use one or more cocatalysts in the production, in accordance with the invention, of amines by hydrogenation of nitriles and imines using hollow Raney catalysts. Suitable cocatalysts are, for example, salts of cobalt, nickel, lanthanum, cerium or yttrium, preferably salts of cobalt and nickel. A preferred amount of cobalt is 0.01–0.5 mol, especially 0.05–0.2 mol Co catalyst per mol of cobalt catalyst. The cocatalyst(s) can be added to the Raney catalyst or the reaction mixture in the form of water-free salts or salts containing water of crystallization, in powder form, as a solution or as a suspension.

Nitriles or imines serve as starting materials for the production of amines in accordance with the invention. The invention additionally includes the production of amines from imines by catalytic hydrogenation in which the imine is formed in situ in the hydrogenation reaction or in which the imine is not formed until immediately before hydrogenation to the amine. For instance, imines can first be produced from aldehydes and ketones in situ in the hydrogenation reactor in the presence of ammonia or primary amines and these aldehydes and ketones can be converted to the desired amine under the given hydrogenation conditions. The imination can also take place immediately before the hydrogenation, so that a more or less complex mixture containing at least one imine is subjected to hydrogenation. This method of processing in accordance with the invention is especially preferred in the production of isophoronediamine in which isophoronenitrileimine is first produced from isophoronenitrile immediately before the hydrogenation or in situ and is then converted to amine by hydrogenation. A corresponding process method is also possible for the production of other amines.

In a preferred embodiment the invention concerns the production of isophoronediamine. It is possible to produce isophoronediamine in one step or in more than one step. If the process is carried out in one step, isophoronenitrile is hydrogenated to produce the amine in the presence of ammonia, hydrogen, a hollow Raney catalyst and optionally other additives. In this case the isophoronenitrileimine is first formed in situ and then hydrogenated.

The term "in more than one step" means that isophoronenitrile is converted entirely or partly to isophoronenitrileimine in a separate reactor or reactor section and this isophoronenitrileimine is subjected to aminating hydrogenation as a pure substance or in a mixture with other components, preferably in the presence of ammonia. The use of the hollow Raney catalyst in accordance with the invention is important in the hydrogenation of the isophoronenitrileimine.

A particularly preferred embodiment of the method in accordance with the invention is the production of isophoronediamine in a two-step process: in the first step at least a part of the isophoronenitrile that is used is converted to isophoronenitrileimine in the presence or absence of an imination catalyst. The ratio of isophoronenitrileimine to isophoronenitrile should be greater than 1, preferably greater than 4 and even more preferably greater than 9 after the imination. In the second step the reaction product of the first step, as it is formed or after further treatment, is hydrogenated in the presence of at least ammonia and hydrogen using hollow Raney catalysts.

The imination can be carried out in the presence or absence of an imination catalyst. If imination is carried out in the absence of an imination catalyst, several hours are needed for a reaction temperature in the range between 10 and about 60° C. to achieve the desired degree of imination. At higher temperatures there is the danger of more severe byproduct formation, which would have a significant adverse effect on the purity of the isophoronediamine end product. Additional processing and purification steps would be necessary.

It is expedient to use an imination catalyst in order to speed up the achievement of equilibrium in the imination reaction. The imination catalysts known from the prior art can be used for this. Suitable catalysts are, for example, inorganic or organic ion exchangers (see EP 0 042 119), supported heteropolyacids (see DE 44 26 472), acid metal oxides, especially aluminum oxide and titanium dioxide (anatas) (see EP 0 449 089), organopolysiloxanes containing sulfonic acid groups (DE 196 27 265.3) and acid zeolites. When an imination catalyst is used, the reaction temperature can lie between 10 and 150° C., preferably between 60 and 130° C. and especially between 80 and 120° C. The imination reaction is preferably carried out at pressures in the range from 2 to 30 MPa.

Although the imination of isophoronenitrile with liquid ammonia is possible in the absence of another solvent, it proved to be advantageous to use in addition a solvent from the series of alcohols with 1–4 C atoms, preferably a monohydric primary alcohol, especially methanol, or a water-soluble ether like tetrahydrofuran or dioxane. Preferably a mixture containing isophoronenitrile, liquid ammonia and methanol is fed to the imination reaction. The mixture expediently contains 10–40 wt %, preferably 10–30 wt % isophoronenitrile and 10–40 wt %, preferably 20–40 wt % ammonia. It is advantageous to mix the isophoronenitrile, ammonia and the solvent together in a ratio so that an essentially homogeneous mixture results. In principle it is possible to go above and below the said limit values, provided an essentially homogeneous solution results when this is done. It is possible through the use of the organic solvent to conduct the imination reaction at lower pressures than would be possible in the absence of the solvent. In the presence of the solvent the preferred pressures lie in the range from 2–10 MPa.

In imination in the presence of an imination catalyst the catalyst can be used in the form of a suspension catalyst or a fixed-bed catalyst. The use of a fixed-bed catalyst is advantageous, since in doing so costly steps for separation of the reaction mixture and the catalyst become unnecessary. In imination of isophoronenitrile in the presence of a fixed-bed catalyst the catalyst is used in the form of conventional catalyst particles such as extruded strands, pellets or tablets as the charge in a fixed-bed reactor. The imination catalyst can be arranged in a reactor of its own. However, it is also possible to arrange the imination catalyst in a reactor that contains both a charge of the imination catalyst and also a charge of the catalyst to be used for the aminating hydrogenation. In each case according to whether the reactor is operated as a trickle bed reactor or a bubble reactor the bed of imination catalyst will be situated above (trickle bed reactor) or below (bubble reactor) the bed of the hydrogenation catalyst. It also proved to be advantageous to use a single reactor that contains a bed of hydrogenation catalyst and also a bed of imination catalyst. In this case the two steps of the isophoronediamine synthesis take place in one reactor, but in two separate reactor sections. Preferably such a reactor is operated in the form of a trickle bed reactor. Here the mixture of isophoronenitrile, ammonia and alcohol, in particular methanol, is fed to the top of the reactor. In these cases hydrogen for the aminating hydrogenation expediently flows simultaneously into the reactor from above.

Catalytic hydrogenation with a hollow Raney catalyst in the production of isophoronediamine is important to the invention. Although basically one can also use Raney catalysts with nickel, copper, iron, palladium or platinum for the hydrogenation, of the described hollow Raney catalysts those based on cobalt and ruthenium are preferred, since in this particular reaction they usually afford better yields. It is also possible that the catalyst contains other catalytically active metals in addition to cobalt and/or ruthenium.

It is preferred that an organic solvent, preferably a $C_1$ to $C_4$ alcohol, especially methanol, or a water-soluble ether, especially tetrahydrofuran, be contained in the mixture containing the isophoronenitrileimine during the production of isophoronediamine. In this case it is possible to conduct the aminating hydrogenation at lower pressures than in the absence of such a solvent. Provided there were no organic solvents in the reaction mixture in the imination carried out in the first step, one can also add an organic solvent, preferably methanol, to the reaction mixture to be subjected to aminating hydrogenation.

However, it is also possible to connect several trickle bed reactors in succession for the hydrogenation, with the reaction mixture leaving the first reactor being sent on to the top of the second reactor. It is possible with this method to subdivide the hydrogenation step further. The construction and mode of operation of such reactors is known from the prior art.

The hydrogen needed for the hydrogenation can be sent to the reactor either in an excess amount, for example, up to 10,000 molar equivalents, or in amounts such that no hydrogen leaves the reactor and has to be recycled. If a solvent is present in the reaction mixture, it is preferable not to supply hydrogen in an excess amount, in order to avoid the technical expenditure for separation of this excess, for condensation of the ammonia and solvent contained in it and for compression of the purified hydrogen. If there is no solvent in the reaction mixture in accordance with the less preferred embodiment, aminating hydrogenation can be carried out with a hydrogen excess from 4.5 to 30 molar equivalents. If the method in accordance with the invention is carried out in a continuous process, the hydrogen can be supplied in cocurrent or countercurrent flow.

If a solvent, for example methanol, is contained in the reaction mixture in the aminating hydrogenation in accordance with the preferred embodiment, aminating hydrogenation can usually be carried out at a temperature in the range from 20 to 150° C., preferably 90 to 130° C. and at a pressure in the range from 0 to 10 MPa, preferably 5–80 MPa, and especially under 8 MPa. Because of the said moderate operating pressures that are possible under the given temperature conditions when the preferred mixture of isophoronenitrile, ammonia, water and solvent is used, the investment is reduced and thus the economy is improved over methods that require higher operating pressures. The said pressure is understood to be the overall pressure, which is composed of the partial pressures of ammonia, hydrogen, $C_1$–$C_4$ alcohol and the other components of the reaction mixture. However, it is also possible to carry out the aminating hydrogenation in other temperature or pressure ranges such as, for example, between 150 and 250° C. or at pressures up to 50 MPa, for example, when the reaction mixture does not contain any organic solvent.

In the hydrogenation of isophoronenitrile, or isophoronenitrileimine, two different stereoisomers can form. It may be preferable to influence the isomer ratio through the choice of a temperature program in the hydrogenation step. For example, it is possible to hydrogenate a mixture containing isophoronenitrile or isophoronenitrileimine at first at a temperature in the range between 20 and 90° C. and then in a following section of the reactor at a temperature in the range between 90 and 150° C., where the temperature difference between the two hydrogenation sections should be at least 30° C. Such a temperature program can be achieved in hydrogenation, for example, by dividing the hydrogenation step into two subsections with separate reactor. In this way it is possible to shift the selectivity in the favor of the cis isomer.

In the production of isophoronediamine the hydrogenation is preferably carried out in the presence of ammonia.

Usually 2 or more mol of ammonia, mostly 5–500 mol of ammonia, are used per mol of nitrile or imine. Expediently the ammonia supply that was present in the preceding production of isophoronenitrileimine can be selected. Ammonia additionally serves for imination as solvent partially or-in the absence of another solvent like methanol or tetrahydrofuran—even entirely.

The necessary volume of fixed-bed catalyst for the hydrogenation step is governed by the LHSV value (liquid hour space velocity), which is dependent on the operating pressure, the temperature and the catalyst activity, that must be maintained in order to achieve as nearly quantitative as possible conversion of the mixture containing isophoronenitrileimine and isophoronenitrile. Usually the LHSV value when using the preferred mixture of isophoronenitrileimine, ammonia, water and solvent, is at least 0.5 $h^{-1}$ and it is preferably in the range from 1 $h^{-1}$ to 4 $h^{-1}$ and even more preferably roughly 2 $h^{-1}$ to 3 $h^{-1}$.

In the embodiment that is especially preferred in accordance with the invention, where in the production of isophoronediamine a trickle bed reactor contains a lower bed of hydrogenation catalyst and an upper bed of imination catalyst, the relevant height of each bed is matched to the corresponding catalyst activity. In this case imination expediently can already be carried out in the presence of hydrogen.

The reaction mixture leaving the hydrogenation reaction in which isophoronediamine is produced is processed further in substantially known ways. This processing usually includes distilling out the ammonia, followed by distilling out the solvents, if the solvents are present, and fractional distillation of the crude product.

It is possible to use cocatalysts, hydroxide bases, especially quaternary alkylammonium hydroxides, in the production of isophoronediamine, as already described in detail above.

The method for producing amines by hydrogenation of nitrites and/or imines with the aid of a hollow Raney catalyst in accordance with the invention has the following advantages:

The hollow Raney catalyst used in accordance with the invention has a clearly lower bulk density than the previously used Raney catalysts. Because of this, considerably less catalyst material than in the previously known methods is required.

In spite of the clearly lower amount of catalyst material the production of amines can be carried out with high conversion rates, very good yields and very good space-time yields.

The catalyst used in the method in accordance with the invention has very good strength. This results in very good hydrogenation reactivity that lasts over a long period of time.

APPLICATION EXAMPLE 1

The catalyst activities of the catalysts from Examples 1–8 were compared in the hydrogenation of butyronitrile to butylamine. For this purpose 20 mL catalyst (from 11 to 41 g of the corresponding catalyst) was charged to a tubular reactor and tested in a trickle phase. The reaction temperature was 75° C., the concentration of butyronitrile in methanol was 20 wt % and the reaction pressure was 40 bar. The hydrogen throughput was 60 L/h and the LHSV was 0.6 $h^{-1}$. The product mixture was analyzed by GC.

EXAMPLE 1

A catalyst was prepared in accordance with DE 197 21 897 A1 containing 50 wt % cobalt and 50 wt % aluminum alloy. A mixture prepared at room temperature and consisting of 15 wt % polyoxymethylene copolymer and 85 wt % of the cobalt/aluminum alloy was extruded in a twin-screw extruder (Werner & Pfleider; model ZSK 30) at a temperature of 190° C. and a mass flow rate of 10 kg/h. The polyoxymethylene copolymer contained 2.7 wt % butanediol formal as comonomer (Ultraform® N2320) and had an MVR (190° C., 2.16 kg) of 6.7–8.5.

To decompose the polyoxymethylene-the base pieces were heated in an oven to 120° C., initially for 10 min. The composition then took place with a continuous increase of temperature from 120 to 280° C. over a period of 90 min. After this time the decomposition was largely complete. Then the temperature was raised to 800° C. for 125 min. The green pieces were calcined at this temperature for an additional 140 min.

After cooling the molded pieces they were activated in sodium hydroxide (20 wt %) at a temperature of 80° C. for a period of 120 min. 20 mL (30.83 g) of this catalyst was tested per Application Example 1 and the results of this test are given in Table 1.

TABLE 1

Test results for Example 1

| Time (h) | Conversion (%) | Selectivity (%) | Activity (mmol butyronitrile/g cat · h) | Activity (mmol butyronitrile/mL cat · h) |
|---|---|---|---|---|
| 1.17 | 67.31 | 92.51 | 2.92 | 4.51 |
| 8.72 | 47.73 | 93.66 | 2.06 | 3.18 |

EXAMPLE 2

A coating solution was prepared by suspending 1730 g 50% Co and 50% Al alloy powder in 1557 mL of an aqueous solution containing about 2 wt % polyvinyl alcohol. This suspension was then sprayed onto 1000 mL polystyrene spheres that had a diameter of about 2 mm while these spheres were being suspended in an upward directed stream of air. 1 L of these spheres were additionally coated with an alloy solution. The solution for the second layer consisted of 1203 g 50% Co and 50% Al alloy powder in 1557 mL of an aqueous solution that contained about 2 wt % polyvinyl alcohol. This suspension was then sprayed onto 1000 mL of the polystyrene spheres precoated with Co/Al indicated above while these spheres were being suspended in an upward directed stream of air (nitrogen and other gases can also be used). After coating the polystyrene spheres with the said solutions the spheres were heated to 500° C. in order to burn out the polystyrene. The Co/Al hollow spheres were then heated to 800° C. The hollow spheres were then activated in 20 wt % sodium hydroxide for about 1.5 h at 80° C. The resulting activated hollow spheres had a diameter of about 3.3 mm and a shell thickness of about 700 µm. 20 mL (14.61 g) of this catalyst was tested per Application Example 1 and the results of this test are presented in Table 2.

TABLE 2

Test results for Example 2

| Time (h) | Conversion (%) | Selectivity (%) | Activity (mmol butyronitrile/g cat · h) | Activity (mmol butyronitrile/mL cat · h) |
|---|---|---|---|---|
| 1.77 | 99.26 | 94.98 | 9.14 | 6.67 |
| 3.63 | 97.98 | 93.27 | 8.91 | 6.51 |
| 5.57 | 95.06 | 92.88 | 8.64 | 6.31 |

EXAMPLE 3

A catalyst was prepared as in Example 2, altering the amount of metal so that 20 mL of the catalyst weighed 11.86 g instead of 14.61 g. 20 mL (11.86 g) of this catalyst was tested per Application Example 1 and the results of this test are presented in Table 3.

TABLE 3

Test results for Example 3

| Time (h) | Conversion (%) | Selectivity (%) | Activity (mmol butyronitrile/g cat · h) | Activity (mmol butyronitrile/mL cat · h) |
|---|---|---|---|---|
| 1.95 | 84.16 | 95.03 | 9.31 | 5.52 |
| 3.83 | 75.70 | 93.61 | 8.61 | 5.02 |
| 5.75 | 72.35 | 93.21 | 8.43 | 5.00 |

EXAMPLE 4

A free-flowing pelletizable catalyst mixture was prepared in accordance with the instructions in EP 0 648 534 A1 for a catalyst consisting of 1000 g 50% Co and 50% Al alloy powder, 150 g pure cobalt powder and 50 g ethylenebisstearoylamide. Tablets 3 mm in diameter and 3 mm thick were pressed from this mixture. The molded tablets were calcined for 2 h at 700° C. After calcination the tablets were activated for 2 h at 80° C. in 20% sodium hydroxide. 20 mL (40.8 g) of this catalyst was tested per Application Example 1 and the results of this test are presented in Table 4.

TABLE 4

Test results for Example 4

| Time (h) | Conversion (%) | Selectivity (%) | Activity (mmol butyronitrile/g cat · h) | Activity (mmol butyronitrile/mL cat · h) |
|---|---|---|---|---|
| 1.73 | 64.23 | 95.47 | 2.13 | 4.35 |
| 6.62 | 57.46 | 91.94 | 1.93 | 3.95 |

EXAMPLE 5

A coating solution was prepared by suspending 1730 g 48.5% Ni, 50.1% Al, 0.9% Cr and 0.5% Fe alloy powder and 130 g pure nickel powder (99% Ni and $d_{50}$=21 µm) in 1557 mL of an aqueous solution containing about 2 wt % polyvinyl alcohol. This suspension was then sprayed onto 1000 mL polystyrene spheres that had a diameter of about 2 mm while these spheres were being suspended in an upward directed stream of air. 1 L of these spheres were additionally coated with an alloy solution. The solution for the second layer consisted of 1203 g 48.5% Ni, 50.1% Al, 0.9% Cr and 0.5% Fe alloy powder and 130 g pure nickel powder (99% Ni and $d_{50}$=21 µm) and 1083 mL of an aqueous solution containing about 2 wt % polyvinyl alcohol. This suspension was then sprayed onto 1000 mL of the polystyrene spheres precoated with Ni/Al/Cr/Fe indicated above while these spheres were being suspended in an upward directed stream of air (nitrogen and other gases can also be used). After coating the polystyrene spheres with the said solutions the spheres were heated to 500° C. in order to burn out the polystyrene. The Ni/Al/Cr/Fe hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.3 mm and a shell thickness of about 700 µm. 20 mL (15.54 g) of this catalyst was tested per Application Example 1 and the results of this test are presented in Table 5.

TABLE 5

Test results for Example 5

| Time (h) | Conversion (%) | Selectivity (%) | Activity (mmol butyronitrile/g cat · h) | Activity (mmol butyronitrile/mL cat · h) |
|---|---|---|---|---|
| 1.83 | 81.05 | 67.56 | 7.10 | 5.51 |
| 5.83 | 87.17 | 63.90 | 7.69 | 5.98 |

EXAMPLE 6

A coating solution was prepared by suspending 1730 g 53% Ni and 47% Al alloy powder and 130 g pure nickel powder (99% Ni and $d_{50}=21$ μm) in 1557 mL of an aqueous solution containing about 2 wt % polyvinyl alcohol. This suspension was then sprayed onto 1000 mL polystyrene spheres that had a diameter of about 2 mm while these spheres were being suspended in an upward directed stream of air. 1 L of these spheres were additionally coated with an alloy solution. The solution for the second layer consisted of 1203 g 53% Ni and 47% Al alloy powder and 130 g pure nickel powder (99% Ni and $d_{50}=21$ μm) and 1083 mL of an aqueous solution containing about 2 wt % polyvinyl alcohol. This suspension was then sprayed onto 1000 mL of the polystyrene spheres precoated with Ni/Al indicated above while these spheres were being suspended in an upward directed stream of air (nitrogen and other gases can also be used). After coating the polystyrene spheres with the said solutions the spheres were heated to 500° C. in order to bum out the polystyrene. The Ni/Al hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.3 mm and a shell thickness of about 700 μm. 20 mL (16.69 g) of this catalyst was tested per Application Example 1 and the results of this test are presented in Table 6.

TABLE 6

Test results for Example 6

| Time (h) | Conversion (%) | Selectivity (%) | Activity (mmol butyronitrile/g cat · h) | Activity (mmol butyronitrile/mL cat · h) |
|---|---|---|---|---|
| 2.47 | 87.98 | 64.77 | 7.17 | 5.99 |
| 6.27 | 88.25 | 59.90 | 7.13 | 5.95 |

EXAMPLE 7

A free-flowing pelletizable catalyst mixture was prepared in accordance with the instructions in EP 0 648 534 A1 for a catalyst consisting of 1000 g 40% Ni, 58.5% Al, 1.0% Cr and 0.5% Fe alloy powder, 75 g pure nickel powder (99% Ni; $d_{50}=21$ μm) and 50 g ethylenebisstearoylamide. Tablets 3 mm in diameter and 3 mm thick were pressed from this mixture. The molded tablets were calcined for 2 h at 700° C. After calcination the tablets were activated for 2 h at 80° C. in 20% sodium hydroxide. 20 mL (25.48 g) of this catalyst was tested per Application Example 1 and the results of this test are presented in Table 7.

TABLE 7

Test results for Example 7

| Time (h) | Conversion (%) | Selectivity (%) | Activity (mmol butyronitrile/g cat · h) | Activity (mmol butyronitrile/mL cat · h) |
|---|---|---|---|---|
| 1.7 | 85.7 | 71.0 | 4.58 | 5.83 |
| 6.2 | 76.7 | 65.8 | 4.06 | 5.18 |

EXAMPLE 8

A coating solution was prepared by suspending 1730 g 53% Ni and 47% Al alloy powder and 130 g pure nickel powder (99% Ni; $d_{50}=21$ μm) in 1557 mL of an aqueous solution containing about 2 wt % polyvinyl alcohol. This suspension was then sprayed onto 1000 mL polystyrene spheres that had a diameter of about 2 mm while these spheres were being suspended in an upward directed stream of air. 1 L of these spheres were additionally coated with an alloy solution. The solution for the second layer consisted of 1203 g 53% Ni and 47% Al alloy powder and 130 g pure nickel powder (99% Ni; $d_{50}=21$ μm) and 1083 mL of an aqueous solution containing about 2 wt % polyvinyl alcohol. This suspension was then sprayed onto 1000 mL of the polystyrene spheres precoated with Ni/Al indicated above while these spheres were being suspended in an upward directed stream of air (nitrogen and other gases can also be used). After coating the polystyrene spheres with the said solutions the spheres were heated to 500° C. in order to bum out the polystyrene. The Ni/Al hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.3 mm and a shell thickness of about 700 μm. This catalyst was doped with a sodium molybdate solution; the end Mo content of the catalyst was 0.3%. 20 mL (18.74 g) of this catalyst was tested per Application Example 1 and the results of this test are presented in Table 8.

TABLE 8

Test results for Example 8

| Time (h) | Conversion (%) | Selectivity (%) | Activity (mmol butyronitrile/g cat · h) | Activity (mmol butyronitrile/mL cat · h) |
|---|---|---|---|---|
| 3.8 | 84.0 | 55.2 | 6.05 | 5.67 |
| 11.7 | 81.3 | 51.7 | 5.95 | 5.58 |

APPLICATION EXAMPLE 2

The catalyst activities of the catalysts from Examples 9 and 10 were compared in the hydrogenation of benzonitrile to benzylamine. For this purpose 20 mL catalyst (from 15 to 41 g of the corresponding catalyst) was charged to a tubular reactor and tested in a trickle phase. The reaction temperature was 75° C., the concentration of benzonitrile in methanol was 20 wt % and the reaction pressure was 40 bar. The hydrogen throughput was 60 L/h and the LHSV was 2 h$^{-1}$. The product mixture was analyzed by GC.

EXAMPLE 9

A free-flowing pelletizable catalyst mixture was prepared in accordance with the instructions in EP 0 648 534 A1 for a catalyst consisting of 1000 g 50% Co and 50% Al alloy powder, 150 g pure cobalt powder and 50 g ethylenebisstearoylamide. Tablets 3 mm in diameter and 3 mm thick were pressed from this mixture. The molded tablets were calcined for 2 h at 700° C. After calcination the tablets were activated for 2 h at 80° C. in 20% sodium hydroxide. 20 mL (40.58 g) of this catalyst was tested per Application Example 2 and the results of this test are presented in Table 9.

EXAMPLE 10

A coating solution was prepared by suspending 1730 g 50% Co and 50% Al alloy powder in 1557 mL of an aqueous solution containing about 2 wt % polyvinyl alcohol. This suspension was then sprayed onto 1000 mL polystyrene spheres that had a diameter of about 2 mm while these spheres were being suspended in an upward directed stream of air. 1 L of these spheres were additionally coated with an alloy solution. The solution for the second layer consisted of 1203 g 50% Co and 50% Al alloy powder in 1557 mL of an aqueous solution that contained about 2 wt % polyvinyl alcohol. This suspension was then sprayed onto 1000 mL of the polystyrene spheres precoated with Co/Al indicated above while these spheres were being suspended in an upward directed stream of air (nitrogen and other gases can also be used). After coating the polystyrene spheres with the said solutions the spheres were heated to 500° C. in order to burn out the polystyrene. The Co/Al hollow spheres were then heated to 800° C. The hollow spheres were then activated in 20 wt % sodium hydroxide for about 1.5 h at 80° C. The resulting activated hollow spheres had a diameter of about 3.3 mm and a shell thickness of about 700 µm. 20 mL (15.76 g) of this catalyst was tested per Application Example 2 and the results of this test are presented in Table 10.

TABLE 9

Test results for Example 9

| Time (h) | Conversion (%) | Selectivity (%) | Activity (mmol benzonitrile/g cat · h) | Activity (mmol benzonitrile/mL cat · h) |
|---|---|---|---|---|
| 1.18 | 87.29 | 91.23 | 8.25 | 16.7 |
| 3.18 | 89.01 | 91.76 | 8.44 | 17.1 |

TABLE 10

Test results for Example 10

| Time (h) | Conversion (%) | Selectivity (%) | Activity (mmol benzonitrile/g cat · h) | Activity (mmol benzonitrile/mL cat · h) |
|---|---|---|---|---|
| 1.67 | 82.37 | 88.15 | 20.29 | 16.0 |
| 3.75 | 83.02 | 89.49 | 19.87 | 15.7 |

APPLICATION EXAMPLE 3

The catalyst activities of the catalysts from Examples 11–17 were compared in the hydrogenation of adiponitrile (ADN) to hexamethylenediamine (HMD) and aminocapronitrile (ACN). For this purpose 40 mL catalyst (from 30 to 83 g of the corresponding catalyst) was charged to a tubular reactor and tested in a trickle phase. The reaction temperature was 110–154° C., the concentration of the adiponitrile in methanol was 20 wt % and the reaction pressure was 65 bar. The hydrogen throughput was 65–129 L/h and the LHSV was 0.13–1.03 h$^{-1}$. The product mixture was analyzed by GC.

EXAMPLE 11

A free-flowing pelletizable catalyst mixture was prepared in accordance with the instructions in EP 0 648 534 A1 for a catalyst consisting of 1000 g 50% Co and 50% Al alloy powder (this alloy was melted in an induction oven and atomized in water), 75 g pure nickel powder (99% Ni; $d_{50}$=21 μm) and 50 g ethylenebisstearoylamide. Tablets 3 mm in diameter and 3 mm thick were pressed from this mixture. The molded tablets were calcined for 2 h at 700° C. After calcination the tablets were activated for 2 h at 80° C. in 20% sodium hydroxide. 40 mL (71.49 g) of this catalyst was tested per Application Example 3 and the results of this test are presented in Table 11.

TABLE 11

Test results for Example 11

| Time (h) | LSHV (1/h) | Temp. (° C.) | Vol H$_2$ (l/h) | Conversion (%) | Selectivity (%) | Activity (mol ADN/g cat · h) | HMD/ACN | Activity (mol ADN/mL cat · h) |
|---|---|---|---|---|---|---|---|---|
| 4.65 | 0.51 | 153.9 | 129 | 96.5 | 40.2 | 0.267 | 2.8 | 0.477 |

EXAMPLE 12

A coating solution was prepared by suspending 1730 g 53% Ni and 47% Al alloy powder and 130 g pure nickel powder (99% Ni and $d_{50}$=21 μm) in 1557 mL of an aqueous solution containing about 2 wt % polyvinyl alcohol. This suspension was then sprayed onto 1000 mL polystyrene spheres that had a diameter of about 2 mm while these spheres were being suspended in an upward directed stream of air. 1 L of these spheres were additionally coated with an alloy solution. The solution for the second layer consisted of 1203 g 53% Ni and 47% Al alloy powder and 130 g pure nickel powder (99% Ni and $d_{50}$=21 μm) and 1083 mL of an aqueous solution containing about 2 wt % polyvinyl alcohol. This suspension was then sprayed onto 1000 mL of the polystyrene spheres precoated with Ni/Al indicated above while these spheres were being suspended in an upward directed stream of air (nitrogen and other gases can also be used). After coating the polystyrene spheres with the said solutions the spheres were heated to 500° C. in order to burn out the polystyrene. The Ni/Al hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.3 mm and a shell thickness of about 700 μm. 40 mL (35.17 g) of this catalyst was tested per Application Example 3 and the results of this test are presented in Table 12.

TABLE 12

Test results for Example 12

| Time (h) | LSHV (1/h) | Temp. (° C.) | Vol H$_2$ (l/h) | Conversion (%) | Selectivity (%) | Activity (mol ADN/g cat · h) | HMD/ACN | Activity (mol ADN/mL cat · h) |
|---|---|---|---|---|---|---|---|---|
| 4.03 | 0.51 | 154.7 | 129 | 98.7 | 25.4 | 0.55 | 5.1 | 0.484 |

EXAMPLE 13

A catalyst was prepared in accordance with Example 2, changing the amount of metal so that 20 mL of the catalyst weighed 12.66 g instead of 14.61 g. 40 mL (25.32 g) of this catalyst was tested per Application Example 3 and the results of this test are presented in Table 13.

TABLE 13

Test results for Example 13

| Time (h) | LSHV (1/h) | Temp. (° C.) | Vol H$_2$ (l/h) | Conversion (%) | Selectivity (%) | Activity (mol ADN/g cat · h) | HMD/ACN | Activity (mol ADN/mL cat · h) |
|---|---|---|---|---|---|---|---|---|
| 2.47 | 1.03 | 114.7 | 129 | 71.4 | 88.2 | 1.02 | 2.2 | 0.708 |
| 3.35 | 0.26 | 110.8 | 65 | 99.9 | 79.8 | 0.39 | 796.0 | 0.247 |

EXAMPLE 14

A free-flowing pelletizable catalyst mixture was prepared in accordance with the instructions in EP 0 648 534 A1 for a catalyst consisting of 1000 g 50% Co and 50% Al alloy powder, 150 g pure cobalt powder and 50 g ethylenebisstearoylamide. Tablets 3 mm in diameter and 3 mm thick were pressed from this mixture. The molded tablets were calcined for 2 h at 700° C. After calcination the tablets were activated for 2 h at 80° C. in 20% sodium hydroxide. 40 mL (82.38 g) of this catalyst was tested per Application Example 3 and the results of this test are presented in Table 14.

TABLE 14

Test results for Example 14

| Time (h) | LSHV (1/h) | Temp. (° C.) | Vol H$_2$ (l/h) | Conversion (%) | Selectivity (%) | Activity (mol ADN/g cat · h) | HMD/ACN | Activity (mol ADN/mL cat · h) |
|---|---|---|---|---|---|---|---|---|
| 2.70 | 1.03 | 112 | 129 | 42.0 | 90.5 | 0.20 | 1.1 | 0.416 |
| 3.97 | 0.26 | 111 | 65 | 86.5 | 84.6 | 0.10 | 5.2 | 0.216 | these spheres were being suspended in an upward directed stream of air (nitrogen and other gases can also be used). After coating the polystyrene spheres with the said solutions the spheres were heated to 500° C. in order to burn out the polystyrene. The Co/Al/Cr/Ni hollow spheres were then heated to 800° C. The hollow spheres were then activated in 20 wt % sodium hydroxide for about 1.5 h at 80° C. The resulting activated hollow spheres had a diameter of about 3.3 mm and a shell thickness of about 700 μm. 40 mL (33.32 g) of this catalyst was tested per Application Example 3 and the results of this test are presented in Table 15.

TABLE 15

Test results for Example 15

| Time (h) | LSHV (1/h) | Temp. (° C.) | Vol H$_2$ (l/h) | Conversion (%) | Selectivity (%) | Activity (mol ADN/g cat · h) | HMD/ACN | Activity (mol ADN/mL cat · h) |
|---|---|---|---|---|---|---|---|---|
| 2.42 | 1.03 | 115 | 129 | 71.8 | 78.4 | 0.85 | 1.3 | 0.711 |
| 4.43 | 0.26 | 112 | 65 | 99.8 | 66.0 | 0.30 | 93.1 | 0.249 |

EXAMPLE 15

A coating solution was prepared by suspending 1730 g 47.4% Co, 50% Al, 1.3% Cr and 1.3% Ni alloy powder in 1557 mL of an aqueous solution containing about 2 wt % polyvinyl alcohol. This suspension was then sprayed onto 1000 mL polystyrene spheres that had a diameter of about 2 mm while these spheres were being suspended in an upward directed stream of air. 1 L of these spheres was additionally coated with an alloy solution. The solution for the second layer consisted of 1203 g 47.4% Co, 50% Al, 1.3% Cr and 1.3% Ni alloy powder in 1557 mL of an aqueous solution that contained about 2 wt % polyvinyl alcohol. This suspension was then sprayed onto 1000 mL of the polystyrene spheres precoated with Co/Al/Cr/Ni indicated above while

EXAMPLE 16

A coating solution was prepared by suspending 1730 g 48.5% Ni, 50.1% Al, 0.9% Cr and 0.5% Fe alloy powder and 130 g pure nickel powder (99% Ni; d$_{50}$=21 μm) in 1557 mL of an aqueous solution containing about 2 wt % polyvinyl alcohol. This suspension was then sprayed onto 1000 mL polystyrene spheres that had a diameter of about 2 mm while these spheres were being suspended in an upward directed stream of air. 1 L of these spheres were additionally coated with an alloy solution. The solution for the second layer consisted of 1203 g 48.5% Ni, 50.1% Al, 0.9% Cr and 0.5% Fe alloy powder and 130 g pure nickel powder (99% Ni; d$_{50}$=21 μm) and 1083 mL of an aqueous solution containing about 2 wt % polyvinyl alcohol. This suspension was then sprayed onto 1000 mL of the polystyrene spheres precoated with Ni/Al/Cr/Fe indicated above while these spheres were being suspended in an upward directed stream of air (nitrogen and other gases can also be used). After coating the polystyrene spheres with the said solutions the spheres were heated to 500° C. in order to burn out the polystyrene. The Ni/Al/Cr/Fe hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.3 mm and a shell thickness of about 700 μm. 40 mL (30.63 g) of this catalyst was tested per Application Example 3 and the results of this test are presented in Table 16.

TABLE 16

Test results for Example 16

| Time (h) | LSHV (1/h) | Temp. (° C.) | Vol $H_2$ (l/h) | Conversion (%) | Selectivity (%) | Activity (mol ADN/g cat · h) | HMD/ACN | Activity (mol ADN/mL cat · h) |
|---|---|---|---|---|---|---|---|---|
| 2.62 | 1.03 | 112.6 | 129 | 51.7 | 61.7 | 0.67 | 1.1 | 0.512 |
| 4.00 | 0.26 | 110.5 | 65 | 88.3 | 43.0 | 0.29 | 4.6 | 0.220 |

EXAMPLE 17

A coating solution was prepared by suspending 1730 g 47.4% Co, 50% Al, 1.3% Cr and 1.3% Ni alloy powder in 1557 mL of an aqueous solution containing about 2 wt % polyvinyl alcohol. This suspension was then sprayed onto 1000 mL polystyrene spheres that had a diameter of about 2 mm while these spheres were being suspended in an upward directed stream of air. 1 L of these spheres were additionally coated with an alloy solution. The solution for the second layer consisted of 1203 g 47.4% Co, 50% Al, 1.3% Cr and 1.3% Ni alloy powder in 1557 mL of an aqueous solution that contained about 2 wt % polyvinyl alcohol. This suspension was then sprayed onto 1000 mL of the polystyrene spheres precoated with Co/Al/Cr/Ni indicated above while these spheres were being suspended in an upward directed stream of air (nitrogen and other gases can also be used). After coating the polystyrene spheres with the said solutions the spheres were heated to 500° C. in order to burn out the polystyrene. The Co/Al/Cr/Ni hollow spheres were then heated to 800° C. The hollow spheres were then activated in 20 wt % sodium hydroxide for about 1.5 h at 80° C. The resulting activated hollow spheres had a diameter of about 3.3 mm and a shell thickness of about 700 μm. This catalyst was doped with an LiOH solution, and the end LiOH content of the catalyst was ~0.2%. 40 mL (31.58 g) of this catalyst was tested per Application Example 3 and the results of this test are presented in Table 17.

TABLE 17

Test results for Example 17

| Time (h) | LSHV (1/h) | Temp. (° C.) | Vol $H_2$ (l/h) | Conversion (%) | Selectivity (%) | Activity (mol ADN/g cat · h) | HMD/ACN | Activity (mol ADN/mL cat · h) |
|---|---|---|---|---|---|---|---|---|
| 2.38 | 1.03 | 113.2 | 129 | 78.3 | 96.4 | 0.98 | 3 | 0.776 |
| 3.60 | 0.26 | 110.7 | 65 | 99.9 | 95.0 | 0.32 | 118 | 0.249 |

APPLICATION EXAMPLE 4

The catalytic activity of the catalysts from Example 18 was compared in the hydrogenation of adiponitrile (ADN) to hexamethylenediamine (HMD) and aminocapronitrile (ACN). For this purpose 40 mL catalyst (30.63 g of the corresponding catalyst) was charged to a tubular reactor and tested in a trickle phase. The reaction temperature was 110–154° C., the concentration of the ADN in methanol was 20 wt %, the NaOH concentration was 1.9 g per liter of the AND+methanol solution, and the reaction pressure was 65 bar. The hydrogen throughput was 65–129 L/h and the LHSV was 0.13–1.03 $h^{-1}$. The product mixture was analyzed by GC.

EXAMPLE 18

A coating solution was prepared by suspending 1730 g 48.5% Ni, 50.1% Al, 0.9% Cr and 0.5% Fe alloy powder and 130 g pure nickel powder (99% Ni; $d_{50}$=21 μm) in 1557 mL of an aqueous solution containing about 2 wt % polyvinyl alcohol. This suspension was then sprayed onto 1000 mL polystyrene spheres that had a diameter of about 2 mm while these spheres were being suspended in an upward directed stream of air. 1 L of these spheres were additionally coated with an alloy solution. The solution for the second layer consisted of 1203 g 48.5% Ni, 50.1% Al, 0.9% Cr and 0.5% Fe alloy powder and 130 g pure nickel powder (99% Ni; $d_{50}$=21 μm) and 1083 mL of an aqueous solution containing about 2 wt % polyvinyl alcohol. This suspension was then sprayed onto 1000 mL of the polystyrene spheres precoated with Ni/Al/Cr/Fe indicated above while these spheres were being suspended in an upward directed stream of air (nitrogen and other gases can also be used). After coating the polystyrene spheres with the said solutions the spheres were heated to 500° C. in order to burn out the polystyrene. The Ni/Al/Cr/Fe hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.3 mm and a shell thickness of about 700 μm. 40 mL (30.63 g) of this catalyst was tested per Application Example 4 and the results of this test are presented in Table 18.

EXAMPLE 19

A coating solution was prepared by suspending 1730 g 50% Co and 50% Al alloy powder in 1557 mL of an aqueous solution containing about 2 wt % polyvinyl alcohol. This suspension was then sprayed onto 1000 mL polystyrene spheres that had a diameter of about 2 mm while these spheres were being suspended in an upward directed stream of air. 1 L of these spheres were additionally coated with an alloy solution. The solution for the second layer consisted of 1203 g 50% Co and 50% Al alloy powder in 1557 mL of an aqueous solution that contained about 2 wt % polyvinyl alcohol. This suspension was then sprayed onto 1000 mL of the polystyrene spheres precoated with Co/Al indicated above while these spheres were being suspended in an upward directed stream of air (nitrogen and other gases can also be used). After coating the polystyrene spheres with the said solutions the spheres were heated to 500° C. in order to burn out the polystyrene. The Co/Al hollow spheres were then heated to 800° C. The hollow spheres were then activated in 20 wt % sodium hydroxide for about 1.5 h at 80° C. The resulting activated hollow spheres had a diameter of about 3.3 mm and a shell thickness of about 700 μm. 11.50 g of this catalyst was tested per Application Example 5 and the catalyst showed an activity of 0.3425 mL $H_2$ absorption per minute with an ADN selectivity of 77%.

EXAMPLE 20

10.10 g of a commercial supported $Co/Al_2O_3$ catalyst was tested per Application Example 5 and the catalyst showed an activity of 0.1952 mL $H_2$ uptake per minute, with an ADN selectivity of 63%.

APPLICATION EXAMPLE 6

The catalytic activity of the catalyst from Example 21 was compared in the hydrogenation of adiponitrile (ADN) to hexamethylenediamine (HMD) and aminocapronitrile (ACN). For this purpose 11.50 g of the catalyst was put into a basket in an autoclave and tested in liquid phase. The reaction temperature was 150° C., the amount of ADN was 30 g, the amount of methanol was 180 g, liquid ammonia was supplied to the reaction in a 5:1 mol ratio to the ADN, the solution was stirred at 1000 rpm and the reaction pressure was 70 bar. The product mixture was analyzed by GC.

TABLE 18

Test results for Example 18

| Time (h) | LSHV (1/h) | Temp. (° C.) | Vol $H_2$ (l/h) | Conversion (%) | Selectivity (%) | Activity (mol ADN/g cat · h) | HMD/ACN | Activity (mol ADN/mL cat · h) |
|---|---|---|---|---|---|---|---|---|
| 2.82 | 1.03 | 115.1 | 129 | 79.1 | 91.3 | 1.02 | 3 | 0.783 |
| 4.17 | 0.26 | 110.8 | 65 | 97.8 | 92.5 | 0.32 | 26 | 0.244 |

APPLICATION EXAMPLE 5

The catalyst activities of the catalysts from Examples 19 and 20 were compared in the hydrogenation of adiponitrile (ADN) to hexamethylenediamine (HMD) and aminocapronitrile (ACN). For this purpose around 10 to 12 g of the catalyst was put into a basket in an autoclave and tested in liquid phase. The reaction temperature was 150° C., the amount of ADN was 30 g, the amount of methanol was 180 g, the solution was stirred at 1000 rpm and the reaction pressure was 75 bar. The product mixture was analyzed by GC.

EXAMPLE 21

A coating solution was prepared by suspending 1730 g 50% Co and 50% Al alloy powder in 1557 mL of an aqueous solution containing about 2 wt % polyvinyl alcohol. This suspension was then sprayed onto 1000 mL polystyrene spheres that had a diameter of about 2 mm while these spheres were being suspended in an upward directed stream of air. 1 L of these spheres were additionally coated with an alloy solution. The solution for the second layer consisted of 1203 g 50% Co and 50% Al alloy powder in 1557 mL of an aqueous solution that contained about 2 wt % polyvinyl alcohol. This suspension was then sprayed onto 1000 mL of the polystyrene spheres precoated with Co/Al indicated above while these spheres were being suspended in an upward directed stream of air (nitrogen and other gases can also be used). After coating the polystyrene spheres with the said solutions the spheres were heated to 500° C. in order to burn out the polystyrene. The Co/Al hollow spheres were then heated to 800° C. The hollow spheres were then activated in 20 wt % sodium hydroxide for about 1.5 h at 80° C. The resulting activated hollow spheres had a diameter of about 3.3 mm and a shell thickness of about 700 μm. 11.50 g of this catalyst was tested per Application Example 5 and the catalyst showed an activity of 0.375 mL $H_2$ uptake per minute, with an ADN selectivity of 92%.

What is claimed is:

1. A method for producing amines comprising catalytically hydrogenating a nitrile or imine with a hydrogen-containing gas in the presence of a molded hydrogenation Raney catalyst, wherein the Raney catalyst is present in the form of hollow bodies.

2. The method as in claim 1, wherein the hollow Raney catalysts contain nickel, cobalt, copper, iron, platinum, palladium, ruthenium or mixtures of these metals as catalytically active components.

3. The method as in claim 1, wherein the Raney catalyst is in the form of hollow spheres.

4. The method as in claim 2, wherein the Raney catalyst is in the form of hollow spheres.

5. The method as in claim 1, wherein the bulk density of the Raney catalyst lies in the range from 0.3 g/mL to 1.3 g/mL.

6. The method as in claim 1, wherein the molded catalyst has a diameter in the range from 0.05 to 20 mm.

7. The method as in claim 1, wherein the molded catalyst has a shell thickness in the range of 0.05–5 mm.

8. The method as in claim 7, wherein the molded catalyst has a shell thickness in the range of 0.1 mm to 5 mm.

9. The method as in claim 1, wherein, the molded catalyst does not contain any binder.

10. The method as in claim 1, wherein the molded catalyst contains an inorganic binder.

11. The method as in claim 1, wherein the catalyst contains cobalt doped with one or more of the elements from groups 3B through 7B, 8 and 1B of the periodic system.

12. The method as in claim 11, wherein the catalyst contains cobalt doped with chromium, manganese, iron, vanadium, tantalum, titanium, tungsten, molybdenum, rhenium and/or metals of the platinum group.

13. The method as in claim 1, wherein the catalyst contains cobalt doped with one or more of the elements from groups 1A, 2A, 2B and/or 3A of the periodic system and/or germanium, tin, lead, antimony or bismuth.

14. The method as in claim 1, further comprising hydrogenating in continuous operation in a fixed bed or suspension reactor.

15. The method as in claim 14, wherein hydrogenating is carried out in a trickle bed process.

16. The method as in claim 1, further comprising having a cocatalyst selected from the group consisting of cobalt and nickel salts present during aminating hydrogenation.

17. The method as in claim 1, wherein that hydrogenating is done in a batch process.

18. The method as in claim 1, wherein a basic material is present in the hydrogenation.

19. The method as in claim 18, wherein the basic material is an alkali hydroxide, alkaline earth hydroxide or ammonium hydroxide.

20. The method as in claim 1, wherein 0–80 wt % ammonia with respect to all of the mixtures sent to hydrogenation is present in the hydrogenation reaction.

21. The method as in claim 1, wherein amines are produced with the formula $R^1R^2CH—NHR^3$, where $R^1$, $R^2$ and $R^3$, independent of one another, are aliphatic, cycloaliphatic and/or aromatic, long-chain and/or branched, substituted and/or unsubstituted, saturated and/or unsaturated residues, or hydrogen.

22. The method as in claim 21, wherein the amines contain two or more amino groups.

23. The method as in claim 21, wherein $R^1$, $R^2$ or $R^3$ are substituted with one or more members selected from the group consisting of F, Cl, Br, I, $NO_2$, $NH_2$, HO, CN, alkyl, aryl, alkenyl, alkynyl, O=C, HOOC, $H_2$NOC, ROOC, RO with R=alkyl, aryl, alkenyl or alkynyl.

24. The method as in claim 21, wherein aliphatic amines of the formula $R^1—CH_2—NH_2$ are obtained as product, where $R_1$ is an organic residue of the formula $H_3C—(CH_2)_n$ and n is a whole number from 1 to 30.

25. The method as in claim 21, wherein aliphatic α,ω-diamines of the formula $H_2N—CH_2—(CH_2)_m—CH_2—NH_2$, in which m is a whole number from 1 to 12 are obtained as product.

26. The method as in claim 25, wherein aliphatic α,ω-diamines of the formula $H_2N—CH_2—(CH_2)_m—CH_2—NH_2$, in which m is a whole number 2, 3, 4, 5 or 6 are obtained as product.

27. The method as in claim 1, wherein the product is one or more of the amines selected from the group consisting of ethylamine, n-propylamine, n-butylamine, n-pentylamine, n-hexylamine, n-heptylamine, n-octylamine, n-nonylamine, n-decylamine, stearylamine, pentenylamine, butynylamine, chloroethylamine, trichloroethylamine, hydroxyethylamine, 3-methoxypropylamine, 1,3-bis(3-aminopropyloxy)-2-propanol, tris(3-aminopropyl)nitromethane, 4-(N,N-dimethylamino)butylamine, 4-(N,N-diethylamino)butylamine, di (3-aminopropyl)ether phenylethylamine, (2-chlorophenyl)methylamine, (2,6-dichlorophenyl) methylamine, 1,3-bis(aminomethyl)benzene, 3-(aminomethyl)benzonitrile, 4-bis(aminomethyl)benzene, 4-(aminomethyl)benzonitrile, tetramethylenediamine, pentamethyolenediamine, hexamethylenediamine, heptamethylenediamine, octamethylenediamine, decamethylenediamine, ω-aminobutyronitrile, ω-aminovalerionitrile, ω-aminocapronitrile, ω-aminoheptanoic acid nitrile, or ω-aminooctanoic acid nitrile, and isophoronediamine.

28. The method for producing hexamethylenediamine (HMD) comprising catalytically hydrogenating adiponitrile with a hydrogen-containing gas in the presence of a molded Raney nickel hydrogenation catalyst in the form of hollow bodies.

29. A method for producing hexamethylenediamine (HMD) comprising catalytically hydrogenating adiponitrile with a hydrogen-containing gas and ammonia in the presence of a molded Raney nickel hydrogenation catalyst in the form of hollow bodies.

30. The method for producing hexamethylenediamine (HMD) as in claim 28, wherein said catalyst contains elements of groups 3B to 7B, 8 and 1B of the periodic system.

31. The method according to claim 30, wherein said elements are selected from the group consisting of chromium, manganese, iron, vanadium, tantalum, titanium, tungsten, molybdenum, rhenium and metals of the platinum group.

32. The method for producing hexamethylenediamine (HMD) as in claim 28, further comprising NaOH or/and LiOH present in the hydrogenating of adiponitrile.

33. The method for producing hexamethylenediamine (HMD) comprising catalytically hydrogenating adiponitrile with hydrogen-containing gases in the presence of a molded Raney nickel hydrogenation catalyst in the form of hollow bodies and containing elements selected from groups 1A, 2A, 2B and/or 3A of the periodic system and/or germanium, tin, lead, antimony or bismuth.

34. The method for producing hexamethylenediamine (HMD) as in claim 30, further comprising ammonia being present.

35. The method for producing hexamethylenediamine (HMD) as in claim 33, further comprising carrying out hydrogenation of adiponitrile with hydrogen-containing gases and ammonia in the presence of a molded Raney nickel hydrogenation catalyst.

36. A method for producing hexamethylenediamine (HMD) by catalytic hydrogenation of adiponitrile with hydrogen containing gases in the presences of a molded cobalt hydrogenation catalyst where the catalyst is present in the form of hollow bodies.

37. The method for producing hexamethylenediamine (HMD) as in claim 36, wherein ammonia is additionally present.

38. The method for producing hexamethylenediamine (HMD) as in claim 36, wherein said catalyst contains an element from groups 3B to 7B, 8 and 1B of the periodic system.

39. The method as in claim 38, wherein said element is a member selected from the group consisting of chromium, manganese, iron, vanadium, tantalum, titanium, tungsten, molybdenum, rhenium and metals of the platinum group.

40. The method for producing hexamethylenediamine (HMD) as in claim 38, wherein NaOH or/and LiOH are also present with the molded cobalt hydrogenation catalyst.

41. The method for producing hexamethylenediamine (HMD) as in claim 36, wherein said Raney contains an element from groups 1A, 2A, 2B and/or 3A of the periodic system and/or germanium, tin, lead, antimony or bismuth.

42. The method for producing hexamethylenediamine (HMD) as in claim 38, wherein ammonia is present with said molded Raney cobalt hydrogenation catalyst.

43. The method for producing hexamethylenediamine (HMD) as in claim 41, wherein ammonia is present with said molded Raney cobalt hydrogenation catalyst.

* * * * *